United States Patent [19]
Alspector

[11] Patent Number: 5,763,264
[45] Date of Patent: Jun. 9, 1998

[54] DEVICE FOR DETECTION OF MICROORGANISMS IN A SAMPLE

[75] Inventor: Benjamin Alspector, Jerusalem, Israel

[73] Assignee: BATEC BioAnalitical Technology, Ltd., Jerusalem, Israel

[21] Appl. No.: 799,268

[22] Filed: Feb. 13, 1997

Related U.S. Application Data

[63] Continuation of Ser. No. 608,676, Feb. 29, 1996, abandoned.

[30] Foreign Application Priority Data

Mar. 2, 1995 [IL] Israel ......... 112842

[51] Int. Cl.⁶ ......... C12M 3/00
[52] U.S. Cl. ......... 435/287.3; 435/288.1; 435/303.1; 435/304.1; 435/309.1; 422/58
[58] Field of Search ......... 435/287.1, 287.3, 435/287.9, 288.1, 303.1, 304.1, 309.1; 422/58

[56] References Cited

U.S. PATENT DOCUMENTS 4,801,547  1/1989  Rosenberg ......... 435/292
5,346,829  9/1994  Alspector ......... 435/294
5,420,018  5/1995  Ricci ......... 435/30

FOREIGN PATENT DOCUMENTS

0557041  2/1993  European Pat. Off. ......... C12M 1/28

Primary Examiner—David A. Redding
Attorney, Agent, or Firm—Steinberg, Raskin & Davidson, P.C.

[57] ABSTRACT

The present invention provides a portable self-contained device for the detection of microorganisms in a sample of a liquid, semi-liquid or solid test material. Within a single hermetically sealable vessel are a combined sampling and assay assembly, with means for withdrawal of a sample from a material to be tested, and means for applying the withdrawn sample or portions thereof to the assay assembly. The combined sampling and assay assembly includes a carrier member having a head portion with a cap for sealing the vessel, a main body portion having at least one surface that bears a culture medium, and a tip portion. A slide on the carrier member is reciprocal between the head portion and the tip, comprising a resilient sleeve with at least one applicator tongue being resiliently biased into contact with the culture medium.

16 Claims, 6 Drawing Sheets

DEVICE FOR DETECTION OF MICROORGANISMS IN A SAMPLE

This application is a continuation of application Ser. No. 08/608,676 filed Feb. 29, 1996, now abandoned.

FIELD OF INVENTION

This invention relates to a portable, self-contained microorganism assay device with means for the withdrawal of a sample from a liquid, semi-liquid or solid test material to be assayed and for culturing the withdrawn sample.

BACKGROUND OF INVENTION

Paddles or dip slides are commonly used for detecting the presence and titers of microorganisms in liquids such as urine. The paddles or dip slides carry a culture medium on one or both sides. They are dipped, removed and then incubated in order to grow any microorganisms present within the sampled liquid.

One of the drawbacks of these devices is that individual colonies are only obtained with in a narrow range of titers of microorganisms present within the fluid. In consequence, cultures frequently provide multiple colonies growing together which hinders isolation and identification.

Moreover, dip slide are only suitable for sampling liquids and are inadequate for the sampling of solid test material. Still further, due the direct contact during sampling between the nutrient on the dip slide and the test material, the latter may be contaminated which, in case of sensitive materials such as food, may have dire consequences.

One way of overcoming this problem is described in U.S. Pat. No. 4,801,547 which provides a transfer member in the form of fiat stick, accommodated between two panels of a folding device, at least one of which carries a culture medium. In operation, the transfer member is dipped into the test liquid while still held between the folders panels. After sampling the transfer member is withdrawn from the folding device and as it moves the picked up sample is spread on the culture medium and is thereby diluted.

One shortcoming of that device is that the inner space between the folded panels communicates with the ambient atmosphere during the entire culturing procedure and as a result, microorganisms other than those obtained from the liquid sample may penetrate from air, settle on the culture medium and grow colonies whereby the results are falsified.

European Patent application EP 557041 discloses another assay device of the kind specified in which a support member that carries on one or two faces a culture medium is held within a cover member so as to be reciprocable between a retracted state in which only the tip projected out of the cover member, and a projecting state in which the culture medium bearing surfaces emerge in full. In operation the device is dipped into the test liquid in its retracted state and is then withdrawn therefrom. This is followed by pushing the support member into the projecting state whereby withdrawn liquid that accumulated at the tip is smeared on the culture medium, whereupon the support member is again retracted and the devices incubated.

Because during dipping the support member remains retracted and thus essentially within the cover member, the latter may and usually is also wetted, which gives rise to uncontrolled incubation conditions and unreliable results. Additionally, this device as well is open to the ambient atmosphere and thus suffers from the same disadvantages as that according to U.S. Pat. No. 4,801,547.

Additional types of microbial assay devices are known, however, they all suffer from disadvantages in that they are exposed to the ambient atmosphere, or that they require more than one vessel to accomplish sampling, assay and isolation of microorganisms from the withdrawn sample.

SUMMARY OF THE INVENTION

It is an object of the present invention to provide an improved assay device of the kind specified, free of the above shortcomings, wherein a single hermetically sealed vessel comprises an assay assembly, means for sampling a test material, and applicator means for applying the withdrawn sample or portions thereof to the assay assembly.

In a preferred embodiment according to the present invention there is provided a portable self-contained microorganism assay device comprising:

an open, hermetically sealable vessel having a bottom at one end, a wall and a neck portion at the opposite end;

a combined sampling and assay assembly accommodated within said sealable assay vessel in a withdrawable fashion and including a carrier member having a head portion with a cap for hermetically sealing said neck portion, a main body portion having at least one surface that bears a culture medium, and a tip portion, and a slide mountable on said carrier member and reciprocal on said carrier member between said head portion and tip, said slide comprising a resilient sleeve with at least one applicator tongue depending therefrom in the direction of said tip and being resiliently biased into contact with said culture medium;

means neat the tip of said carrier member for engaging said sleeve when the sampling and assay assembly is pulled out of the vessel; and retainer means for retaining said slide within said neck portion when the combined sampling and assay assembly is introduced into the vessel after sampling.

The term "hermetically sealed" used herein in relation to the sealing of the assay vessel by the cap, means that under normal atmospheric pressure there occurs no significant movement of air between the vessel's interior and the surrounding atmosphere.

In the following, the invention will be described with reference to its application to the assay of liquid test materials, it being understood that it is applicable in a fully analogous fashion also to assaying semi-liquid and solid test materials.

In the non-operative assembled state of the device, the slide is positioned inside the vessel remote from the vessel's neck portion with said at least one applicator tongue being clear of any culture medium. Accordingly, for assembling the device, the slide is first positioned in the manner specified, following which the carrier member is introduced into the vessel so as to engage the slide whereupon the cap is fastened on the vessel's neck portion.

For sampling, the sealing cap is loosened and the combined sampling and assay assembly is pulled out and withdrawn. During withdrawal, the slide is engaged by the carrier member whereby the combined sampling and assay assembly is fully withdrawn. During the entire operation the culture medium remains untouched by the applicator tongues.

The sampling and assay assembly is now dipped into a test liquid to be assayed By a first mode, only the applicator tongues are immersed so that the entire culture medium bearing surface remains unwetted and by an alternative, second mode, also part of the culture medium distal from said head portion is immersed and wetted to form on the culture medium a dipping zone. According to the operator's choice, an assay device according to the invention may be operated in accordance with said first mode or in accordance with said second mode.

Upon reinsertion of the combined sampling and assay assembly into the vessel, the said retainer means retain the slide in the vessel's neck portion and the slide slides as it were on the carrier member as the latter is reintroduced into the vessel. During such sliding, each applicator tongue glides on an associated culture medium surface thereby smearing some of the withdrawn liquid sample on the culture medium to produce thereon a longitudinal, stripe-shaped wetted zone which, depending on whether the dipping was done in accordance with said first or second mode, either begins at the edge of the culture medium bearing surface or the edge of the dipping zone. In each of the so-formed stripe-shaped wetted zones, the concentration of microorganisms diminishes in the direction of the head portion. In case of the existence of a dipping zone, the latter bears part of the withdrawn liquid sample in its original concentration.

In accordance with a first design of a device according to the invention, in the inoperative state the sleeve of the slide is located at allocation on the carrier member that is intermediary between the head portion and tip, and means are provided for creating friction between the sleeve and vessel. In this design, when the sampling and assay assembly is pulled out of the assay vessel, the slide is first retained in its position inside the vessel until engaged by the engagement means near the tip of the carrier member.

In accordance with one embodiment of said first design, said means for causing friction between the sleeve and the vessel comprise at least one resilient protrusion on the outer face of the sleeve bearing with a bias on the vessel wall.

In accordance with another embodiment of said first design, said means for causing friction between the sleeve and the vessel comprise at least one resilient protrusion on the inner face of the vessel wall bearing with a bias on the sleeve.

In accordance with a further embodiment of said first design, said means for causing friction between the sleeve and the vessel comprise at least one resilient protrusion on each of the sleeve and the inner face of the vessel wall bearing with a bias on, respectively, the vessel wall and sleeve.

According to a still further embodiment of said first design, the said means for causing friction between the sleeve and the vessel are provided by the sleeve being, a resilient open ring whose size when relaxed is larger than the inner size of the vessel, whereby when the slide is inserted into the vessel there occurs friction between it and the sleeve.

If desired, arresting means may be provided on the inner face of the vessel wall for cooperation with said stop means of the carrier member so as to arrest the latter in the inoperative state in a position in which the tip remains clear of said at least one applicator tongue. In addition, or in the alternative, further arresting means may be provided for cooperation with said sleeve for arresting the slide in a position in which the said applicator tongues remain clear of the bottom of the vessel.

In accordance with a second design of a device according to the invention, in the inoperative state the sleeve of the slide is retained near the tip of the carrier member. In this design, when the sampling and assay assembly is pulled out of the assay vessel, the slide is pulled with it from the beginning.

Each of the sleeve and the carrier member may be cylindrical, oval or prismatic, e.g. with a trihedral, tetrahedral or other polyhedral shape.

If desired, the culture medium covers only a portion of each face of the carrier, member to which it is applied, leaving a medium free-zone near the head portion. In this way, when upon sampling the combined sampling and assay assembly is fully reinserted into the vessel, the tip of each applicator tongue is clear of the culture medium and is retained in the medium free zone.

In accordance with a preferred embodiment of the invention, the medium free-zone comprises a recess in association with each applicator tongue such that upon complete reinsertion of the combined sampling and assay assembly into the vessel, each applicator tongue snaps into the associated recess whereby any back sliding of the slide is prevented. In accordance with this preferred embodiment, each recess also serves as a trap for liquid, thereby preventing any residual sampling test liquid that remained on the applicator tongue from dipping on to the culture medium whereby falsification of the assay results is avoided.

In accordance with another preferred embodiment according to the present invention, different culture media are present on different faces of the carrier member.

In accordance with yet another preferred embodiment of the present invention, one or more faces of the carrier member that are covered with culture medium may be subdivided so that a different type of culture medium is present in each subdivision. Such subdivisions may be made parallel to the longitudinal axis of the carrier member, perpendicular to it or in any other suitable arrangement.

It is thus seen that, in the device according to the invention one and the same assembly serves for sampling, for spreading sampled liquid on the culture medium, and for the growth of microorganisms. Moreover, due to the fact that in operation the vessel is hermetically sealed by means of the cap of the combined sampling and assay assembly, the microorganisms' growth occurs in isolation from the ambient atmosphere which ensures that the assay results are not falsified by foreign microorganisms.

The hermetic sealing of the vessel after sampling and during the entire incubation, further facilitates compliance with safety procedures enabling sampled material to be transported and incubated within the vessel and thereby avoiding risk of environmental contamination.

If desired, the culture medium of the carrier member may be protected with a disposable guard which is removed prior to use.

In accordance with one embodiment of the invention the sampling and assay assembly is inserted freely into the vessel. Alternatively, guide means may be provided on the inner side of the vessel wall whereby the said assembly is inserted into the vessel at a predetermined angular position. In such an embodiment, the sealing cap must be rotatably mounted on the carrier member.

In certain embodiments wherein the invention is intended for use with liquid or semi-liquid samples, it is also possible to have the applicator means bearing the resilient applicator tongues mounted on the internal surface of the sealable vessel rather than on the assay assembly. In such embodiments the applicator means may be mounted in a fixed position on the internal surface of the sealable vessel, close to the neck portion of said vessel.

According to one such embodiment the assay assembly bearing the culture medium will be withdrawn from the vessel in a first orientation where the surfaces bearing the culture medium do not contact the applicator means, and will be reinserted into the vessel in a second orientation where the surfaces bearing the culture medium are brought into contact with the applicator means. In such embodiments, the assay assembly will be withdrawn from the vessel, part of the culture medium proximal to its tip portion will be immersed to form a dipping zone, and during reinsertion of the assay assembly into the vessel the applicator means will operate in a fashion fully analogous to that wherein the slidable means are mountable on the assay assembly.

BRIEF DESCRIPTION OF THE DRAWINGS

For better understanding the invention will now be described, by way of example only, with reference to the annexed drawings in which.

DETAILED DESCRIPTION OF THE INVENTION

The portable microorganism assay device according to the invention shown in FIGS. 1 to 5 comprises a sealable cylindrical vessel 1 which in the particular embodiment here shown has the shape of a test tube with an inverted conical bottom portion, but which may also have any other suitable shape.

Figures 1, 2:
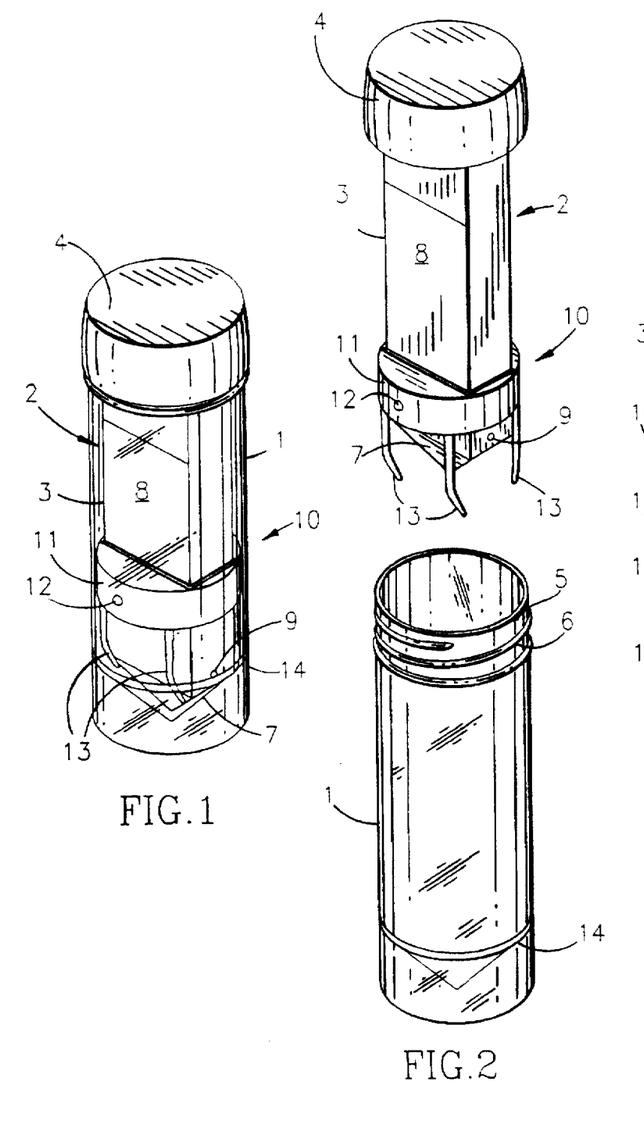
FIG. 1 is a perspective view illustrating an embodiment of a device according to the invention of the first design group, in the sealed inoperative state.
FIG. 2 is a perspective view showing separately the withdrawn sampling and assay assembly and the vessel of the device of FIG. 1.

The device further comprises a combined sampling and assay assembly 2 which includes a substantially flat tetrahedral prismatic carrier member 3 having a head portion with a sealing cap 4 which, as may be desired, is either rigidly or rotatably mounted on the carrier member 3. Vessel 1 has a neck portion 5 with a screw threading 6, and cap 4 has on its inner side a matching screw threading (not shown) whereby the cap 4 is capable of hermetically sealing vessel 1.

In the embodiment of the invention here shown, the surface of the two opposite wide sides of the carrier member 3 are assumed to bear each a culture medium 8. It should, however, be noted that if desired, only one surface or alternatively three or even all four surfaces of the carrier member 3 may each bear a culture medium 8. The culture medium on each surface may be the same or different from that on any other surface. Furthermore, each surface may be subdivided to accommodate more than one culture medium on said surface.

Near its tip 7 carrier member 3 comprises two stops 9 (only one of which is shown).

Slidably mounted on the carrier member 3 of the sampling and assay assembly 2 is a slide 10 comprising a sleeve 11 fitted with a resiliently compressible protrusion 12 bearing with a bias on the vessel wall and thus causing, friction between slide 10 and the vessel. Slide 10 has two pairs of resilient applicator tongues 13 depending therefrom in direction of the tip 7 of carrier member 3, one pair being associated with the first culture medium 8 and the other with the second culture medium (not shown) on the other side of the carrier member. As shown, tongues 13 are bent and the tips thereof are resiliently biased on to the carrier member 3 as they come into contact with it when the slide 10 is driven from the tip 7 to the cap 4. Slide 10 is reciprocal on the main body portion of the carrier member 3, between the head and tip portions thereof.

Near its bottom, vessel 1 comprises an inner rib 14 which serves for arresting the carrier member in a position in which the tips of applicator tongues 13 remain clear of the bottom of vessel 1 so that any damage to the tongues is avoided.

For assembling the device, the slide 10 is first inserted by itself into vessel 1 with the applicator tongues 13 entering first, and the slide is depressed towards the bottom such that the applicator tongues 13 project in direction of the bottom. Once the slide 10 has reached its ultimate position, the carrier member 3 is introduced into the vessel to be received by the slide 10 whereby without the resilient applicator tongues 13 coming into contact with the first and second culture mediums 8, the slide becomes mounted on the carrier member 3. Any undesired depression of slide 10 in consequence of the insertion of the carrier member 3 is avoided by stops 9 abutting rib 14 and as a result the tips of applicator tongues 13 remain clear of the bottom of vessel 1. When the carrier member is fully inserted, the device is sealed by screwing cap 4 on to neck portion 5 of vessel 1.

On withdrawal of the combined sampling and assay assembly 2 from vessel 1, the slide 10 is first retained in position by the friction between the resilient protrusion 12 and the vessel, while the carrier member is pulled out, and as a result, tongues 13 do not come into contact with the culture mediums 8. Once the stops 9 abut the lower edge of sleeve 11, slide 10 engaged by the carrier member 3 and is pulled out together with it, whereby the entire sampling and assay assembly is withdrawn from vessel 1, ready for sampling, and in this operative state slide 10 is situated near the tip of the carrier member 3.

Figure 3:
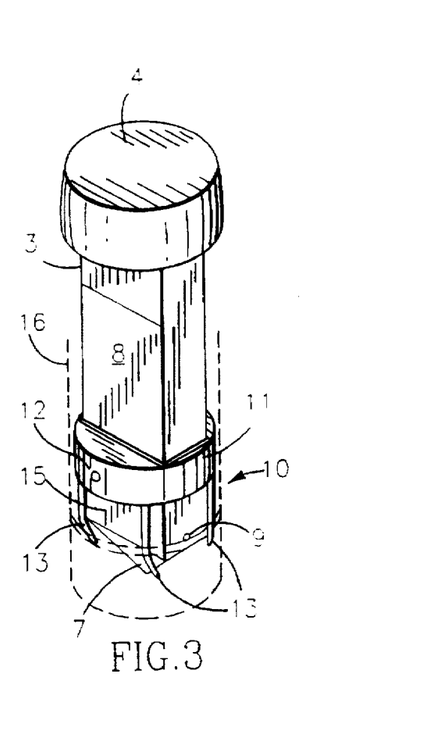
FIG. 3 is a perspective view showing the sampling and assay assembly of the device of FIG. 1 during the sample withdrawing operation.
Figure 4:
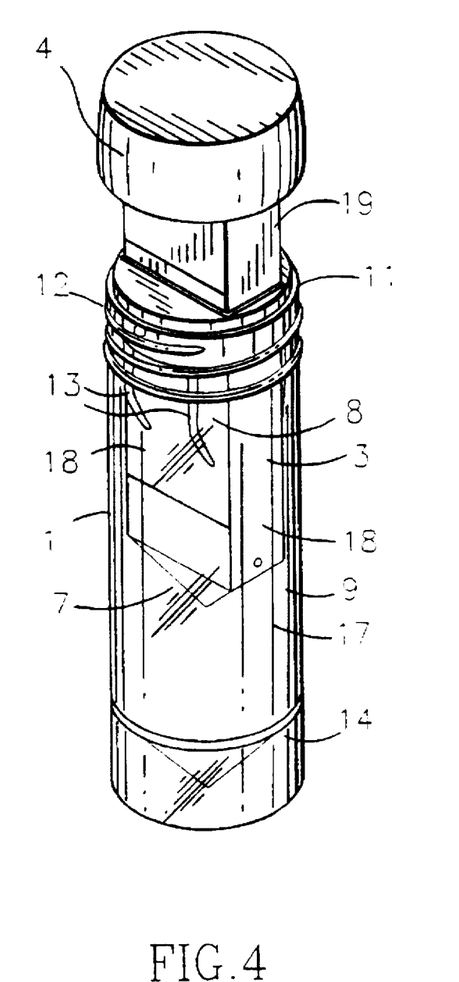
FIG. 4 is a perspective view showing in the device of FIG. 1 an intermediary phase of the reinsertion of the sampling and assay assembly into the vessel.

For the purpose of sampling, the withdrawn sampling and assay assembly 2 is dipped into a body of the test liquid, e.g.

the liquid body 15 inside the container 16. At the option of the operator, dipping is effected by the said first mode in which only applicator tongues 13 are dipped while the entire carrier member 3 remains unwetted, or in accordance with said second mode in which a portion of the carrier member is also dipped whereby a dipping zone is formed close to tip 7, as shown in FIG. 3. The wetted sampling and assay device is withdrawn from the liquid body 15 and is reinserted into vessel 1. FIG. 4 shows an intermediary state of the assembly 2 in the course of reinsertion into vessel 1, and FIG. 5 the final, incubation state.

As shown, the carrier member 3 has a wet dipping zone 17 which remains intact, while beyond that zone the applicator tongues 13 spread the sampled liquid on the culture medium, giving rise to the formation on each culture medium surface of two stripe-like wet zones 18 in which the concentration of microorganisms diminishes in the direction of cap 4. As further seen in FIGS. 4 and 5, during reinsertion of assembly 2, slide 10 is retained near the neck portion of vessel 1, which is due to the friction created by the resilient protrusion 12.

Figure 5:
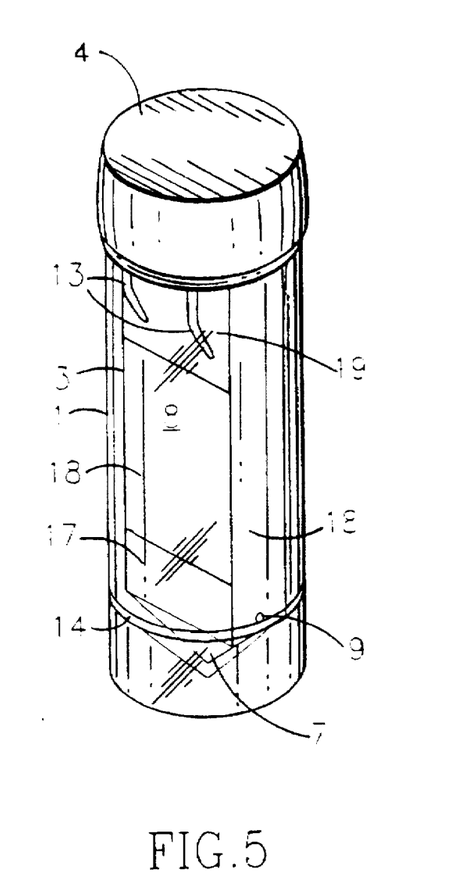
FIG. 5 is a perspective view slowing the vessel of FIG. 1 in the operative sealed state in the course of incubation.
Figures 6, 7, 8:
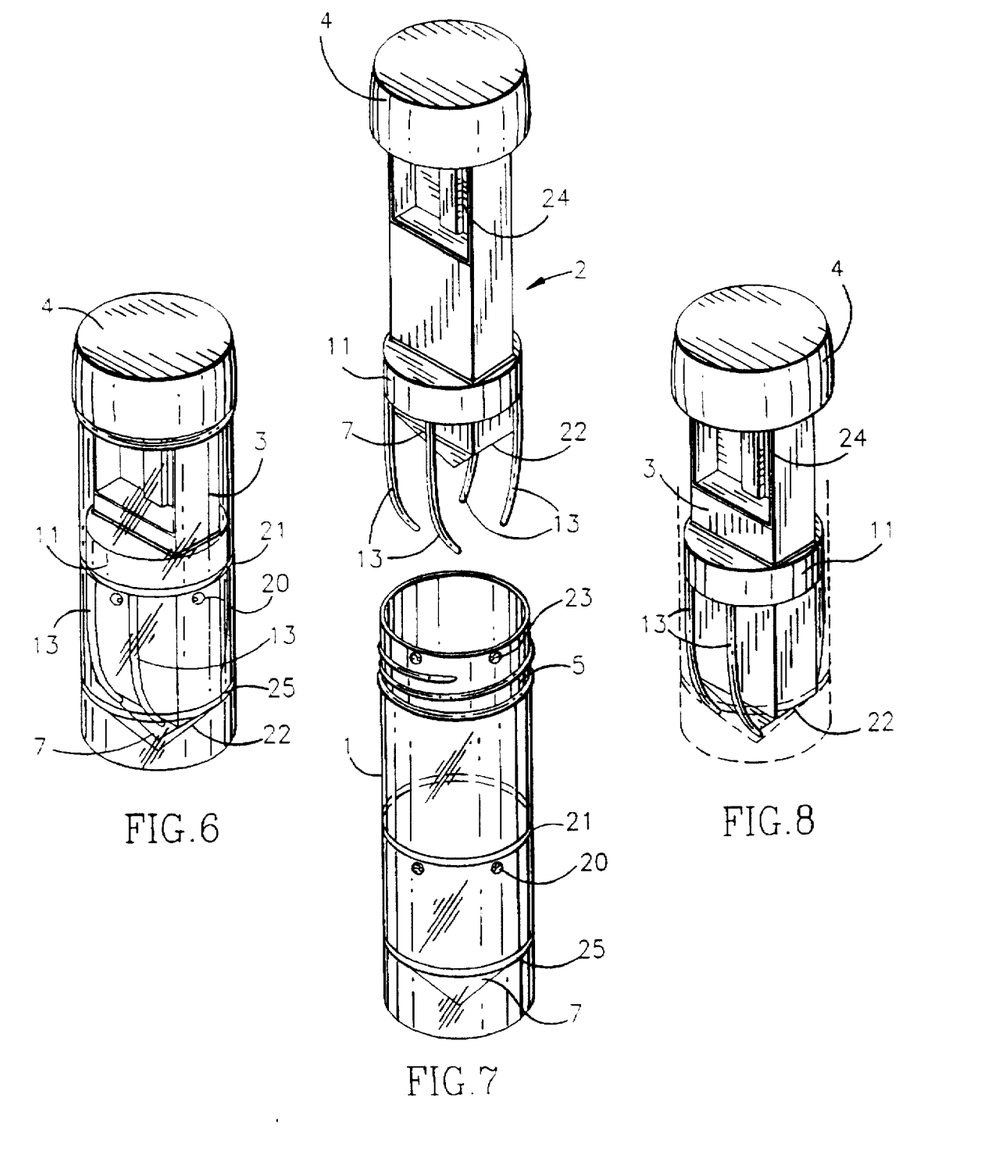
FIG. 6 is a perspective view illustrating another embodiment of a closed device according to the invention of the first design group, in the sealed inoperative state.
FIG. 7 is a perspective view showing separately the withdrawn sampling and assaying assembly and the vessel of the device of FIG. 6.
FIG. 8 is a perspective view showing the sampling and assay assembly of the device of FIG. 6 during the sample withdrawing operation.
Figure 9:
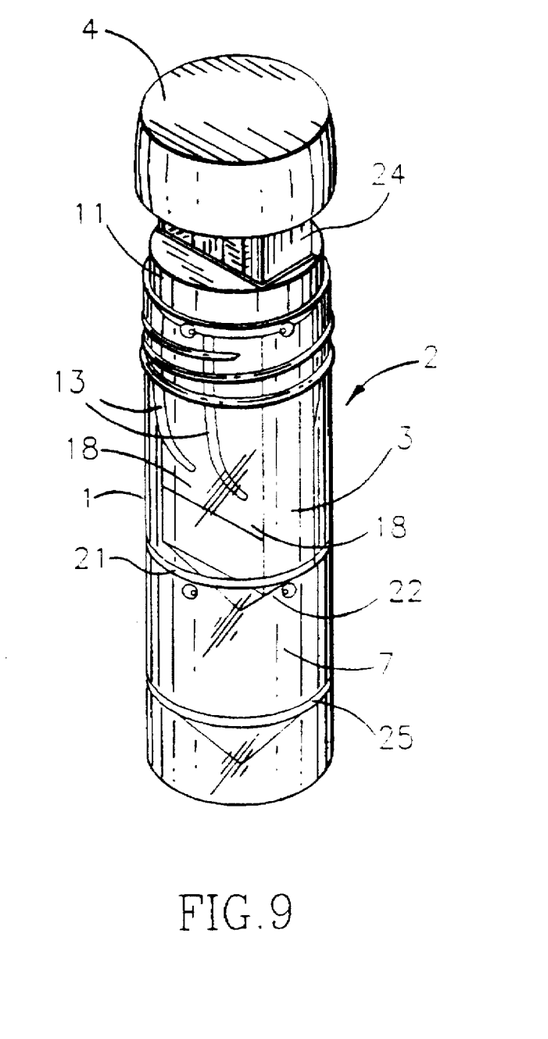
FIG. 9 is a perspective view showing in the device of FIG. 6 an intermediary phase of the reinsertion of the sampling and assay assembly into the incubation vessel.
Figure 10:
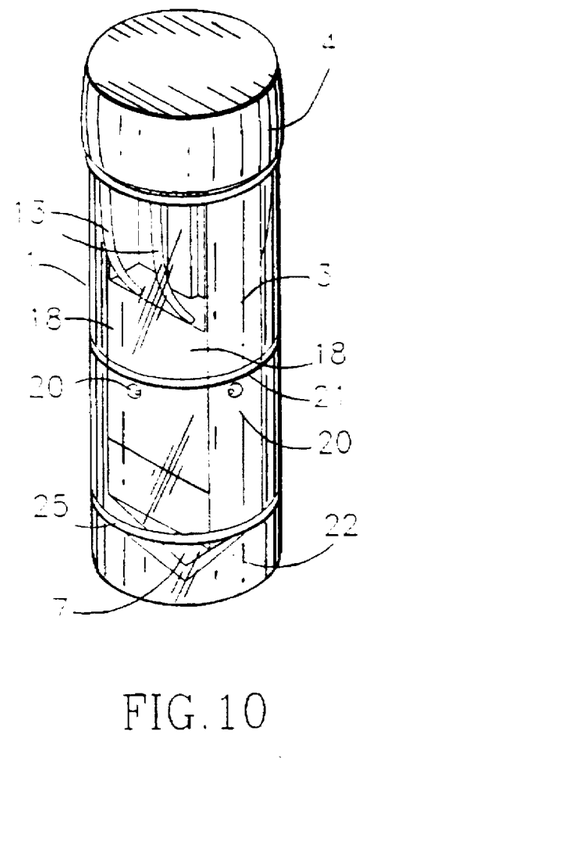
FIG. 10 is a perspective view showing the vessel of FIG. 6 in the operative, sealed state in the course of incubation.
Figures 11, 12:
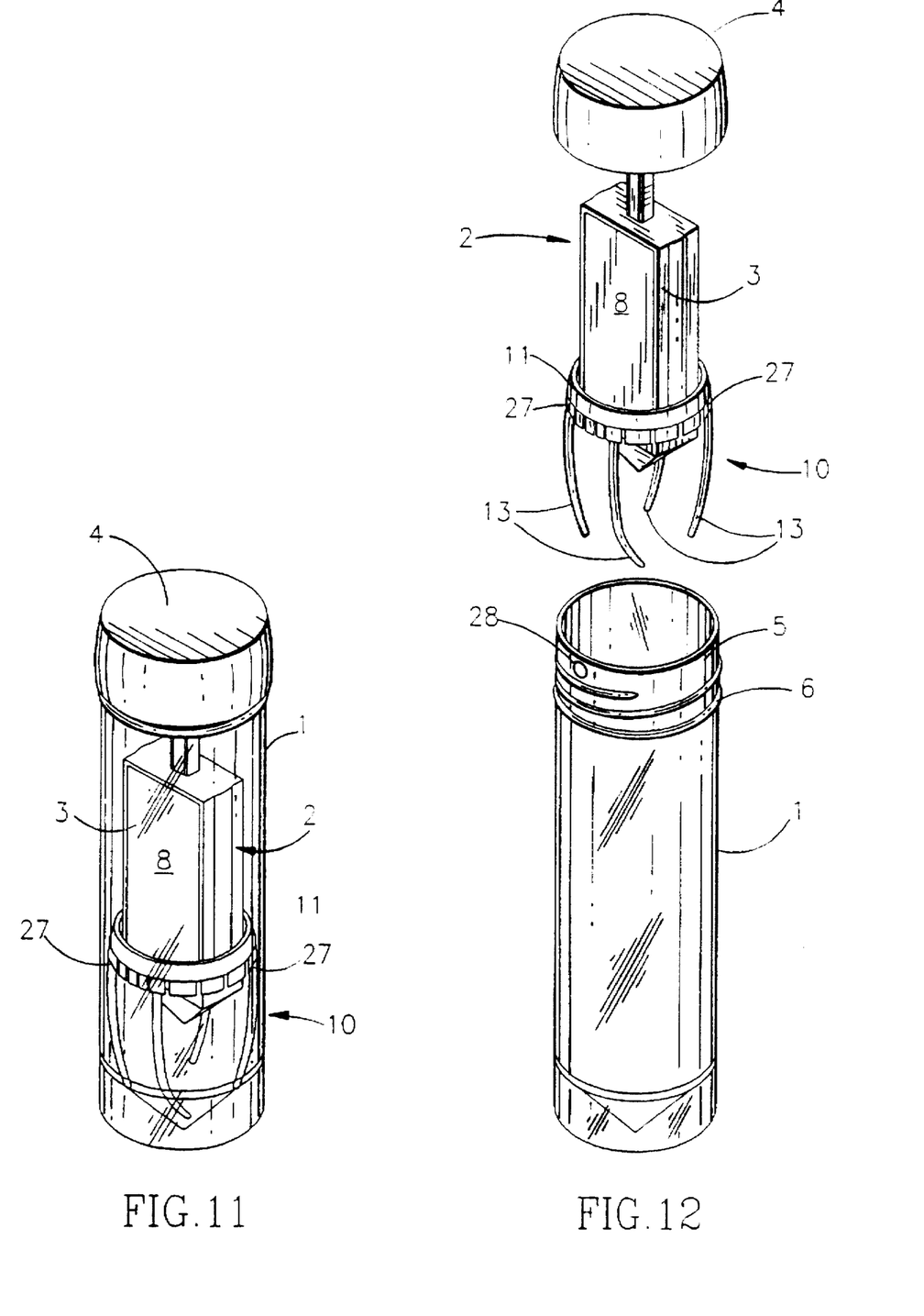
FIG. 11 is a perspective view illustrating an embodiment of a device according to the invention of the second design group in the sealed, inoperative state.
FIG. 12 is a perspective view showing separately the withdrawn sampling and assaying assembly and the vessel of the device of FIG. 11.
Figure 13:
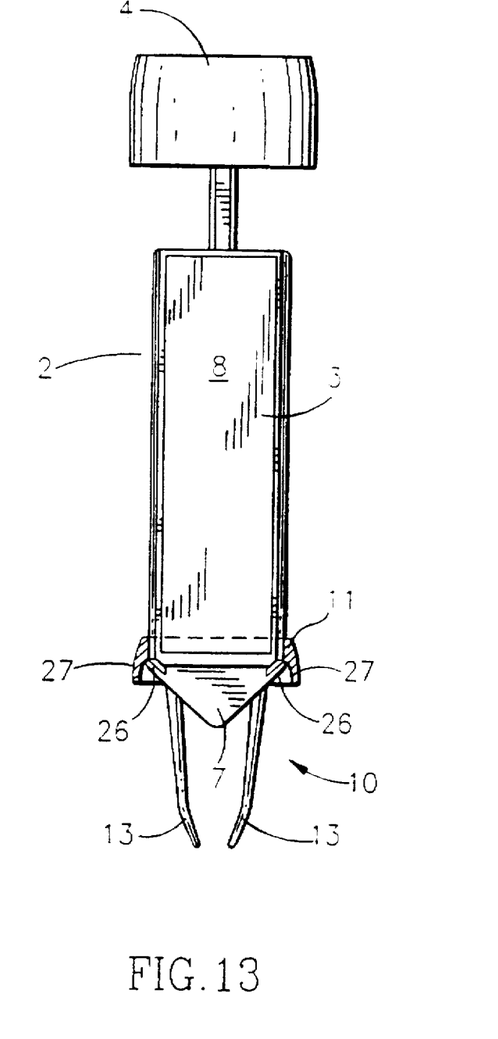
FIG. 13 is a plan view, partially sectional, of the sampling and assay assembly of the device of FIG. 11.
Figure 14:
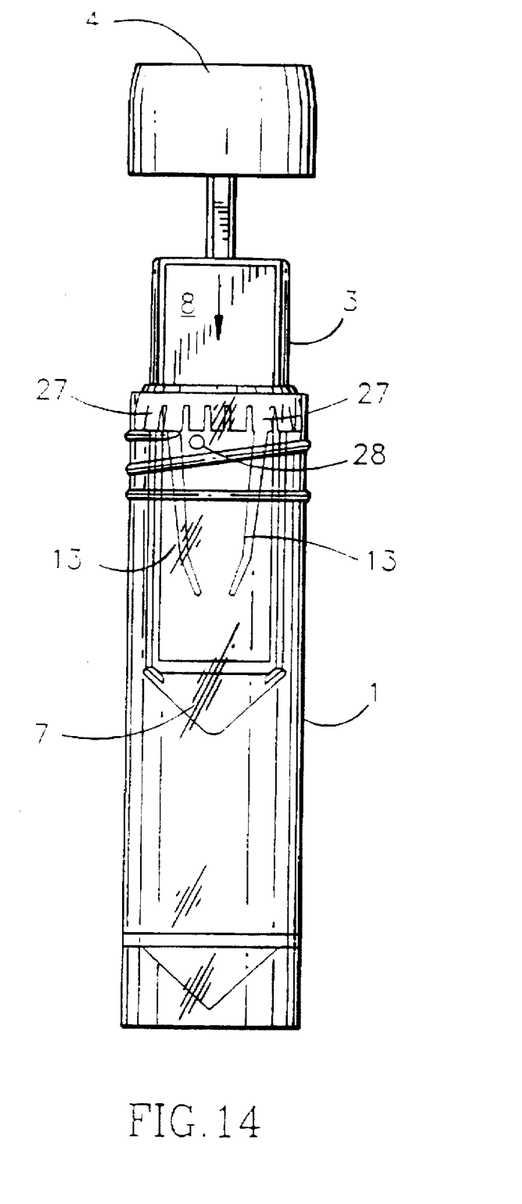
FIG. 14 is a perspective view showing in the device of FIG. 11 an intermediary phase of the reinsertion of the sampling and assay assembly into the vessel.

The culture medium 8 does not extend over the entire length of the bearing surface and a culture medium free-zone 19 is provided between the cap 4 and the culture medium 8 on which the applicator tongues 13 come to rest when the assembly is fully reinserted.

The device is now incubated to allow the growth of colonies of microorganisms. By withdrawing assembly 2 grown colonies can be selectively removed from the carrier member 3 for further culturing and studies. Since, on withdrawal of the sampling and assay assembly 2 after incubation slide 10 remains in its position underneath the cap 4, the culture media 8 are not damaged by tongues 13.

The portable microorganism assay device according to the invention shown in FIGS. 6 to 10 contain all the main features indicated in the embodiment detailed above and illustrated in FIGS. 1 to 5, with the exception that the means for causing friction comprise a plurality of bulges 20 on the inner face of the vessel 1 at about half height and bulges 23 on the inner face of the vessel near the neck portion 5. The bulges 23 resiliently bias on to the sleeve 11 of the slide 10 when in the uppermost position and bulges 20 act in a similar way when the slide 10 is at its lowermost portion.

As seen in FIG. 9, when after sampling the assembly 2 is reinserted into the vessel 1, the plurality of bulges 23 come into frictional contact with the sleeve 11 of the slide 10 whereby the latter is retained in neck portion 5 of the vessel 1 whilst the carrier member 3 is fully inserted into the vessel 1. During reinsertion, the two pairs of resilient applicator tongues 13 each give rise to the formation of two stripe-like wetting zones 18 in which like before, the levels of microorganisms diminish in the direction of the cap 4.

As shown in this embodiment the pair of stop members 22 (one being shown) are located at the tip portion of the carrier member 3 and are designed to abut an internal rib 25 whereby the slide is arrested on insertion into the vessel in a position in which the applicator tongues 13 remain clear of the bottom of vessel 1 whereby the applicator tongues 13 are protected from damage. In the alternative or in addition, sleeve 11 is arrested by a circumferential rib 21.

In this embodiment each culture medium bearing surface of the carrier member 3 comprises near the head portion a pair of recesses 24. Each of the recesses 24 serves as a catch for an associated applicator tongue 13 so that once the tongues have snapped into their catches, the slide 10 can no longer be moved back towards the tip 7, and in this way any risk that the applicator tongues 13 should slide back and damage the culture media and more particularly the zones 18 of diminishing concentration of microorganisms, is eliminated. Recesses 24 also serve as traps for any residual sampled liquid remaining on the applicator tongues 13, whereby any dripping of residual liquid on the culture medium is prevented.

In all other respects the use and operation of this embodiment of the device is the same as that described for the previous embodiment of the invention as illustrated; in FIGS. 1 to 5.

It is thus seen that the portable microorganisms assay device according to the invention affords a number of advantages over the prior art:

(i) it is a compact unit in which one and the same assembly serves for sampling and for growth (ii) if desired, some sampled liquid may retain its original concentration on the culture medium while another part is spread to form zones of diminishing concentration, which enables assays to be performed within a wide range of microorganism titers in the test liquid (iii) after sampling, during handling, transport, incubation, and storage the growth medium is sealed off from the ambient atmosphere which ensures that the results are not falsified by the growth of foreign microorganisms and that risk of environmental contamination is prevented.

FIGS. 11 to 14 show an embodiment of a device according to the invention of the second design group. Essentially this device is similar to those of the first design group shown in FIGS. 1 to 5 and 6 to 10. However, in distinction from those devices, in this case in the sealed, inoperative state the resilient components are in the relaxed state which has the advantage that their resilience is not impaired during storage. Thus, as shown sleeve 11 of slide 10 is retained near tip 7 of carrier member 3, with teeth 26 engaging into the sleeve in the manner shown in FIG. 13. As further shown ring 11 has a skirt consisting of a plurality of dentils 27 which are essentially in the relaxed state and serve to guide slide 10 smoothly along the wall of vessel 1 during withdrawal.

In the neck portion 5 of vessel 1 there are provided a number of inner protrusions 28 which serve to retain slide 10 in the neck portion when the sampling and assay assembly 2 is reintroduced into vessel 1, as shown in FIG. 14.

The operation of the device of FIGS. 11 to 14 is similar to that of the devices of FIGS. 1 to 5 and 6 to 10, but in this case only the applicator tongues 13 are dipped into the test liquid with the consequence that in this case the culture media 8 are not wetted during dipping and thus no dipping zone is formed thereon. Furthermore, due to the fact that sleeve 11 and dentils 27 were in the relaxed state during the entire storage, their resilience remains unimpaired. This ensures that when the sampling and assay assembly 2 is fully withdrawn sleeve 11 and dentils 27 are fully relaxed so that upon reinsertion into vessel 1, sleeve 11 hooks on to protrusions 28 as designed.

Each of the aforementioned embodiments according to the invention may further comprise guide means to retain the resilient sleeve in a predetermined orientation relative to the carrier member. The guide means may, for example comprise at least one recessed groove on the internal surface of the sleeve, in parallel to the longitudinal axis of the carrier member, and a matching projection along at least one face of said carrier member.

It will be appreciated that yet other configurations of the device are within the scope of the invention, including, but not limited, to further embodiments wherein the applicator means are mountable on the internal surface of the sealable vessel, rather than on the combined sampling and assay assembly. This type of device will operate in analogous fashion to that of the exemplary embodiments wherein the applicator means form part of the combined sampling and assay assembly. It is understood that when the applicator means are retained within the vessel, the device will be utilized for liquid samples such that a wetting zone will be formed proximal to the tip end of the assay assembly. The applicator means will distribute the sample from the wetting zone towards the cap end, upon reinsertion of the withdrawn assay assembly into the vessel.

What is claimed is:

1. A portable microorganisms assay device comprising:

an open, sealable assay vessel having a bottom and a wall with a neck portion extending therefrom;

a combined sampling and assay assembly accommodated within the vessel in a withdrawable fashion and including a carrier member having a head portion with a cap for sealing said neck portion of the vessel, a main body portion having at least one surface that bears a culture medium, and a tip portion, and a slide mounted on said carrier member and reciprocal on said carrier member between said head portion and tip;

said slide comprising a sleeve with at least one applicator tongue depending therefrom in direction of said bottom and designed for resilient bias on to said culture medium;

means for engaging said sleeve when the sampling and assay assembly is pulled out of the vessel; and retainer means for retaining said slide within said neck portion when the combined sampling and assay assembly is introduced into the vessel after sampling.

2. The device of claim 1, wherein in the inoperative state the sleeve of the slide is located at a location on the carrier member that is intermediary between the head portion and tip, and means are provided for creating friction between the sleeve and vessel.

3. The device of claim 2, wherein said means for causing friction between the sleeve and the vessel comprise at least one resilient protrusion on the outer face of the sleeve bearing with a bias on the vessel wall.

4. The device of claim 2, wherein said means for causing friction between the sleeve and the vessel comprise at least one resilient protrusion on the inner face of the vessel wall bearing with a bias on the sleeve.

5. The device of claim 2, wherein said means for causing friction between the sleeve and vessel comprise at least one resilient protrusion on each of the sleeve and the inner face of the vessel wall bearing with a bias on, respectively, the vessel and the sleeve.

6. The device of claim 2, wherein said vessel is cylindrical.

7. The device of claim 2 wherein the sleeve is in form of an open ring whose size when relaxed is larger than the inner size of the vessel, whereby when the slide is inserted into the vessel there occurs friction between the sleeve and vessel.

8. The device of claim 2, wherein means are provided on the inner face of the vessel wall for arresting the slide so that the applicator tongues remain clear of the bottom of the vessel.

9. The device of claim 2, wherein the vessel comprises means on the inner face of the wall for engagement by stop means of the carrier member, whereby the latter is arrested in a position in which the tip remains clear of the applicator tongues on the slide.

10. The device of claim 1, wherein in the inoperative state the sleeve of the slide is retained near the tip of the carrier member.

11. The device of claim 10, wherein said vessel is cylindrical.

12. The device of claim 1, wherein each culture bearing medium surface has a culture medium free zone near the head portion of the carrier member.

13. The device of claim 1, wherein the said carrier member comprises near the head portion recesses for snapping engagement by the applicator tongues.

14. The device of claim 1, wherein said culture medium is covered by a removable and disposable guard.

15. The device of claim 1, wherein said cap is rotatably mounted on the carrier member.

16. The device of claim 1, wherein said means is provided on the inner side of the vessel wall whereby the said sampling and assay assembly is inserted into the vessel at a predetermined angular position.

* * * * *